United States Patent
Brannan (10) Patent No.: US 9,526,577 B2
(45) Date of Patent: Dec. 27, 2016

(54) APPARATUS, SYSTEM AND METHOD FOR PERFORMING AN ELECTROSURGICAL PROCEDURE

(71) Applicant: COVIDIEN LP, Mansfield, MA (US)

(72) Inventor: Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/842,199

(22) Filed: Sep. 1, 2015

(65) Prior Publication Data

US 2015/0366614 A1 Dec. 24, 2015

Related U.S. Application Data (62) Division of application No. 12/944,951, filed on Nov. 12, 2010, now Pat. No. 9,119,647.

(51) Int. Cl.
*A61B 18/18* (2006.01)
*A61B 18/00* (2006.01)

(52) U.S. Cl.
CPC .. *A61B 18/1815* (2013.01); *A61B 2018/00023* (2013.01); *A61B 2018/1861* (2013.01); *A61B 2018/1884* (2013.01)

(58) Field of Classification Search
CPC ............... A61B 18/18; A61B 18/1815; A61B 2018/00023; A61B 2018/1861; A61B 2018/1884
USPC ...................................... 606/33–41
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 5,800,494 A | 9/1998 | Campbell et al. |
| D424,694 S | 5/2000 | Tetzlaff et al. |
| D425,201 S | 5/2000 | Tetzlaff et al. |
| 6,289,249 B1 | 9/2001 | Arndt et al. |
| D449,886 S | 10/2001 | Tetzlaff et al. |
| D457,958 S | 5/2002 | Dycus et al. |
| D457,959 S | 5/2002 | Tetzlaff et al. |
| 6,512,956 B2 | 1/2003 | Arndt et al. |
| 6,592,579 B2 | 7/2003 | Arndt et al. |
| 6,675,050 B2 | 1/2004 | Arndt et al. |
| 6,740,108 B1 | 5/2004 | Just et al. |

(Continued)

FOREIGN PATENT DOCUMENTS

| | | |
|---|---|---|
| CN | 1103807 A | 6/1995 |
| DE | 390937 C | 3/1924 |

(Continued)

OTHER PUBLICATIONS

U.S. Appl. No. 12/722,034, filed Mar. 11, 2010, Casey M. Ladtkow.

(Continued)

*Primary Examiner* — Michael Peffley
*Assistant Examiner* — Khadijeh Vahdat (57) ABSTRACT

An apparatus for performing a microwave ablation procedure is provided. The apparatus includes a catheter including an open proximal end and a closed distal end configured to percutaneously access tissue. A directional microwave antenna probe adapted to connect to a source of microwave energy selectively couples to the catheter. The directional microwave antenna is rotatable within the catheter for directing the emission of microwave energy therefrom to tissue.

15 Claims, 5 Drawing Sheets

(56) References Cited

U.S. PATENT DOCUMENTS

| | | |
|---|---|---|
| 6,780,180 B1 | 8/2004 | Goble et al. |
| D496,997 S | 10/2004 | Dycus et al. |
| D499,181 S | 11/2004 | Dycus et al. |
| 7,033,352 B1 | 4/2006 | Gauthier et al. |
| D525,361 S | 7/2006 | Hushka |
| D531,311 S | 10/2006 | Guerra et al. |
| 7,115,126 B2 | 10/2006 | Berube et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| 7,301,131 B2 | 11/2007 | Gauthier et al. |
| 7,303,560 B2 | 12/2007 | Chin et al. |
| D564,662 S | 3/2008 | Moses et al. |
| D606,203 S | 12/2009 | Husheer et al. |
| D613,412 S | 4/2010 | DeCarlo |
| 7,819,866 B2 | 10/2010 | Bednarek |
| 9,119,647 B2 | 9/2015 | Brannan |
| 2001/0008966 A1 | 7/2001 | Arndt et al. |
| 2002/0087151 A1 | 7/2002 | Mody et al. |
| 2006/0009756 A1 | 1/2006 | Francischelli et al. |
| 2009/0295674 A1 | 12/2009 | Bonn |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 836 868 A2 | 4/1998 |
| EP | 0 882 955 A1 | 12/1998 |
| EP | 1159926 A3 | 3/2003 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 8-56955 | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2001231870 A | 8/2001 |
| JP | 2004024787 A | 1/2004 |
| JP | 2005512668 A | 5/2005 |
| JP | 2008142467 A | 6/2008 |
| JP | 2009-285463 A | 12/2009 |
| SU | 166452 | 1/1965 |
| SU | 401367 A1 | 10/1973 |
| SU | 727201 A2 | 4/1980 |
| WO | 2010/035831 A1 | 4/2010 |

OTHER PUBLICATIONS

U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/859,841, filed Aug. 20, 2010, Roman Turovskiy.
U.S. Appl. No. 12/861,333, filed Aug. 23, 2010, Joseph D. Brannan.
U.S. Appl. No. 12/877,182, filed Sep. 8, 2010, Robert B. Cunningham.
U.S. Appl. No. 12/910,442, filed Oct. 22, 2010, Robert B. Cunningham.
U.S. Appl. No. 12/917,053, filed Nov. 1, 2010, Ronald J. Podhajsky.
Japanese Office Action Application No. 2011-247231 dated Feb. 17, 2015.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.

(56) References Cited

OTHER PUBLICATIONS

European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
U.S. Appl. No. 08/136,098, filed Oct. 14, 1993, Roger A. Stern.
U.S. Appl. No. 08/483,742, filed Jun. 7, 1995 Roger A. Stern.
U.S. Appl. No. 12/436,237, filed May 6, 2009, Ronald J. Podhajsky.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.

(56) References Cited

OTHER PUBLICATIONS

Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
U.S. Appl. No. 12/436,239, filed May 6, 2009, Ronald J. Podhajsky.
U.S. Appl. No. 12/472,831, field May 27, 2009, Joseph D. Brannan.
U.S. Appl. No. 12/475,082, filed May 29, 2009, Darion Peterson.
U.S. Appl. No. 12/476,960, filed Jun. 2, 2009, Mani N. Prakash.
U.S. Appl. No. 12/487,917, filed Jun. 19, 2009, Joseph D. Brannan.
U.S. Appl. No. 12/493,302, filed Jun. 29, 2009, Darion Peterson.
U.S. Appl. No. 12/504,738, filed Jul. 17, 2009, Robert J. Behnke.
U.S. Appl. No. 12/535,851, filed Aug. 5, 2009, Joseph D. Brannan.
U.S. Appl. No. 12/535,856, filed Aug. 5, 2009, Joseph D. Brannan.
U.S. Appl. No. 12/536,616, filed Aug. 6, 2009, Arnold V. DeCarlo.
U.S. Appl. No. 12/542,348, filed Aug. 17, 2009, Joseph D. Brannan.
U.S. Appl. No. 12/542,785, filed Aug. 18, 2009, Joseph D. Brannan.
U.S. Appl. No. 12/547,155, filed Aug. 25, 2009, Robert J. Behnke.
U.S. Appl. No. 12/548,644, filed Aug. 27, 2009, Darion Peterson.
U.S. Appl. No. 12/555,576, filed Sep. 8, 2009, Kenlyn S. Bonn.
U.S. Appl. No. 12/556,010, filed Sep. 9, 2009, Ian S. Smith.
U.S. Appl. No. 12/556,238, filed Sep. 9, 2009, Kenlyn S. Bonn.
U.S. Appl. No. 12/561,096, filed Sep. 16, 2009, Kenlyn S. Bonn.
U.S. Appl. No. 12/562,575, filed Sep. 18, 2009, Joseph D. Brannan.
U.S. Appl. No. 12/562,842, filed Sep. 18, 2009, Robert J. Behnke.
U.S. Appl. No. 12/566,299, filed Sep. 24, 2009, Richard A. Willyard.
U.S. Appl. No. 12/568,067, filed Sep. 28, 2009, Francesca Rossetto.
U.S. Appl. No. 12/568,524, filed Sep. 28, 2009, Kenlyn S. Bonn.
U.S. Appl. No. 12/568,551, filed Sep. 28, 2009, Joseph D. Brannan.
U.S. Appl. No. 12/568,777, filed Sep. 29, 2009, Kenlyn S. Bonn.
U.S. Appl. No. 12/568,838, filed Sep. 29, 2009, Kenlyn S. Bonn.
U.S. Appl. No. 12/568,883, filed Sep. 29, 2009, Joseph D. Brannan.
U.S. Appl. No. 12/568,972, filed Sep. 29, 2009, Joseph D. Brannan.
U.S. Appl. No. 12/569,171, filed Sep. 29, 2009, Joseph D. Brannan.
U.S. Appl. No. 12/569,685, filed Sep. 29, 2009, Joseph D. Brannan.
U.S. Appl. No. 12/582,857, filed Oct. 21, 2009, Charles D. Allen.
U.S. Appl. No. 12/606,769, filed Oct. 27, 2009, Joseph D. Brannan.
U.S. Appl. No. 12/607,221, filed Oct. 28, 2009, Joseph D. Brannan.
U.S. Appl. No. 12/607,268, filed Oct. 28, 2009, Joseph D. Brannan.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.

(56) References Cited

OTHER PUBLICATIONS

U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
International Search Report corresponding to European Application No. EP 11009036.2-2305 dated Jul. 4, 2012.
Extended European Search Report corresponding to EP 11 009 036.2, dated Feb. 13, 2012 (5 pp).
European Office Action corresponding to EP 11 009 036.2, dated Jul. 4, 2012 (4 pp).
European Search Report for European Application No. 11009036.2 dated Feb. 1, 2012.

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.

(56) References Cited

OTHER PUBLICATIONS

Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vase. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.

APPARATUS, SYSTEM AND METHOD FOR PERFORMING AN ELECTROSURGICAL PROCEDURE

CROSS-REFERENCE TO RELATED APPLICATIONS

This application is a divisional application of U.S. application Ser. No. 12/944,951, filed on Nov. 10, 2010, now U.S. Pat. No. 9,119,647, the entire contents of which are incorporated by reference herein.

BACKGROUND

Technical Field

The present disclosure relates to an apparatus, system and method for performing an electrosurgical procedure. More particularly, the present disclosure relates to an apparatus, system and method including a directional microwave antenna probe and a catheter that are configured to perform a microwave ablation procedure.

Description of Related Art

Microwave ablation procedures, e.g., such as those performed for menorrhagia, are typically done to ablate the targeted tissue to denature or kill the tissue. Many procedures and types of devices utilizing electromagnetic radiation therapy are known in the art. Such microwave therapy is typically used in the treatment of tissue and organs such as the prostate, heart, and liver. One non-invasive procedure generally involves the treatment of tissue (e.g., a tumor) underlying the skin via the use of microwave energy. Typically, microwave energy is generated by a power source, e.g., microwave generator, and transmitted to tissue via a microwave antenna that is fed with a coaxial cable that operably couples to a radiating section of the microwave antenna.

To treat the tissue, the radiating section of the microwave antenna may be positioned inside the tissue of interest, e.g., the tumor, and microwave energy may be radiated thereabout. Typically, the microwave energy radiates with no specific directionality pattern, i.e., the direction of the microwave energy is not controlled. For example, under certain surgical environments, the microwave energy may radiate radially outward in a generally spherical pattern. While this spherical pattern of microwave energy may be suitable for treating certain shapes and/or types of tissue specimens, e.g., tissue specimens that exhibit a generally spherical shape, under certain circumstances, this spherical pattern of microwave energy may not be suitable for treating other shapes and/or types of tissue specimens, such as, for example, in the instance where the tumor is elongated or otherwise shaped.

SUMMARY

The present disclosure provides a system for performing a microwave ablation procedure. The system includes a catheter including an open proximal end and a closed distal end configured to percutaneously access tissue. A directional microwave antenna probe adapted to connect to a source of microwave energy selectively couples to the catheter. The directional microwave antenna is rotatable within the catheter for directing the emission of microwave energy therefrom to tissue.

The present disclosure provides an apparatus for performing a microwave ablation procedure. The apparatus includes a catheter including an open proximal end and a closed distal end configured to percutaneously access tissue. A directional microwave antenna probe adapted to connect to a source of microwave energy selectively couples to the catheter. The directional microwave antenna is rotatable within the catheter for directing the emission of microwave energy therefrom to tissue.

The present disclosure also provides method of performing a microwave procedure. The method includes percutaneously accessing tissue with a catheter including an open proximal end and a closed distal end configured to percutaneously access tissue for adjacent placement thereto. A step of the method includes positioning a directional microwave antenna probe adapted to connect to a source of microwave energy into the catheter. The directional microwave antenna is rotatable within the catheter for directing the emission of microwave energy therefrom to tissue. And, transmitting microwave energy to the microwave antenna such that a desired tissue effect may be achieved is another step of the method.

BRIEF DESCRIPTION OF THE DRAWING

Various embodiments of the present disclosure are described hereinbelow with references to the drawings, wherein.

FIG. $4B_{-1}$ is a schematic view illustrating another angle of the opening of the directional probe.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end that is closer to the user, while the term "distal" will refer to an end that is farther from the user.

Figure 1A:
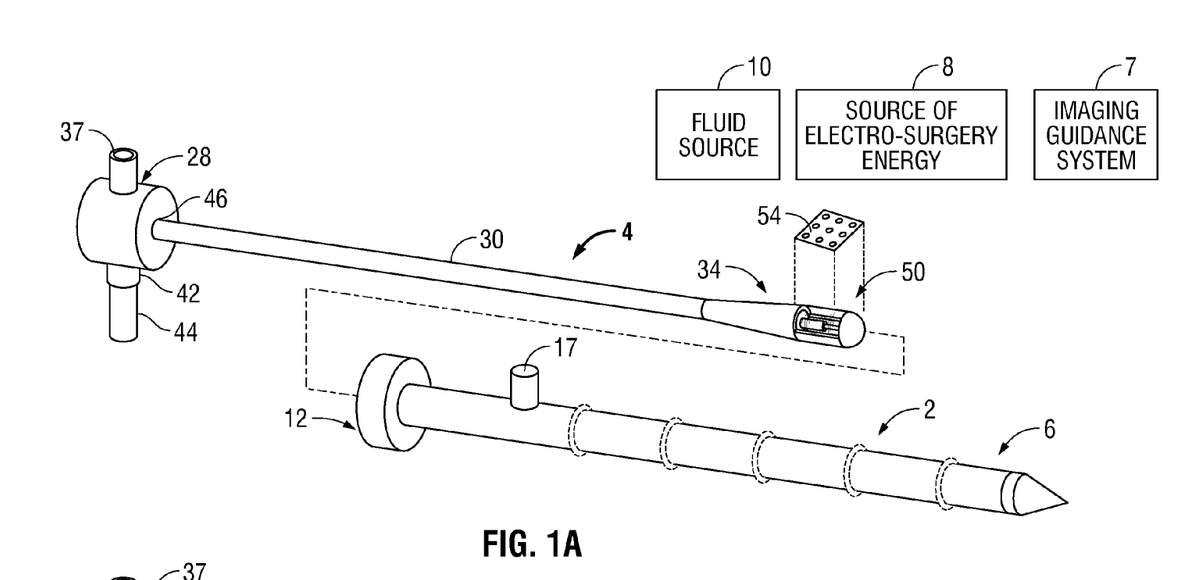
FIG. 1A is a side, perspective view of a system including a directional probe and an introducer catheter according to an embodiment of the present disclosure.
Figure 1B:
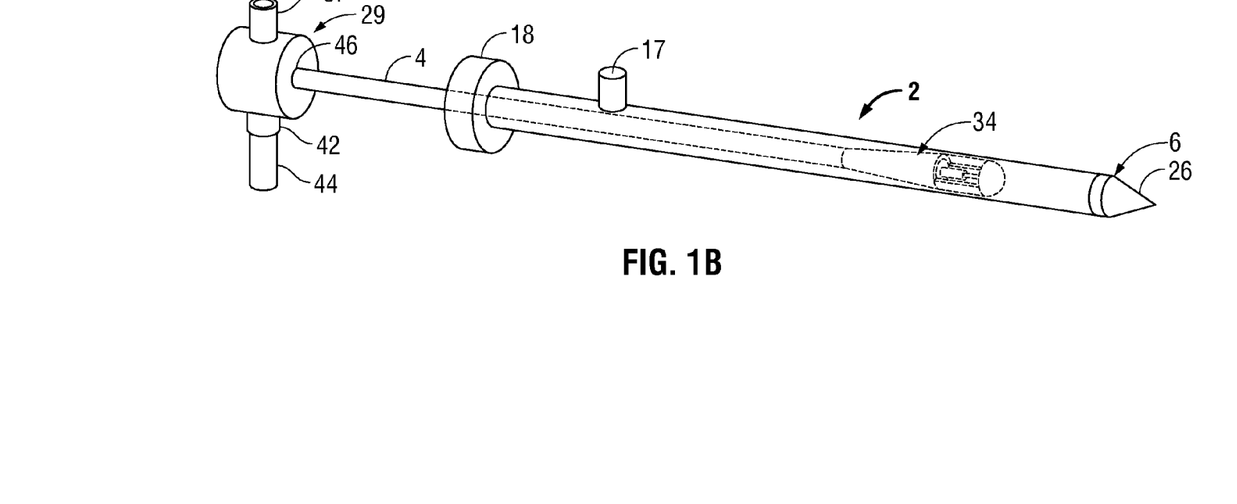
FIG. 1B is a side, perspective view of the system depicted in FIG. 1A with the directional probe coupled to the introducer catheter.

With reference to FIGS. 1A and 1B, a system for performing an electro surgical procedure is designated 2. System 2 includes a directional microwave probe 4 and a catheter 6. Probe 4 is adapted to connect to one or more suitable electrosurgical energy sources, e.g., a microwave generator 8. In certain embodiments the probe 4 and catheter 6 are both adapted to couple to one or more fluid sources 10 that are configured to supply fluid to one or both of the probe 4 and catheter 6. In certain embodiments, the probe 4 and catheter 6 are both adapted to couple to one or more imaging guidance systems 7 that are configured to facilitate positioning the catheter 6 and/or probe 4 disposed therein adjacent tissue.

Figure 2:
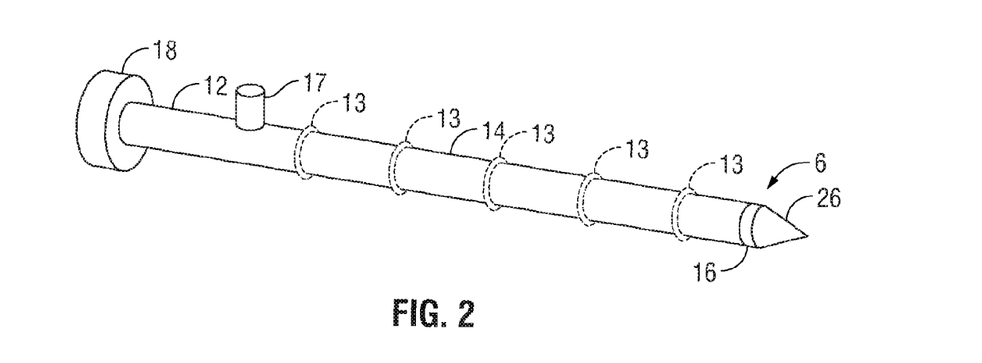
FIG. 2 is a perspective view of the introducer catheter depicted in FIGS. 1A and 1B.
Figure 3:
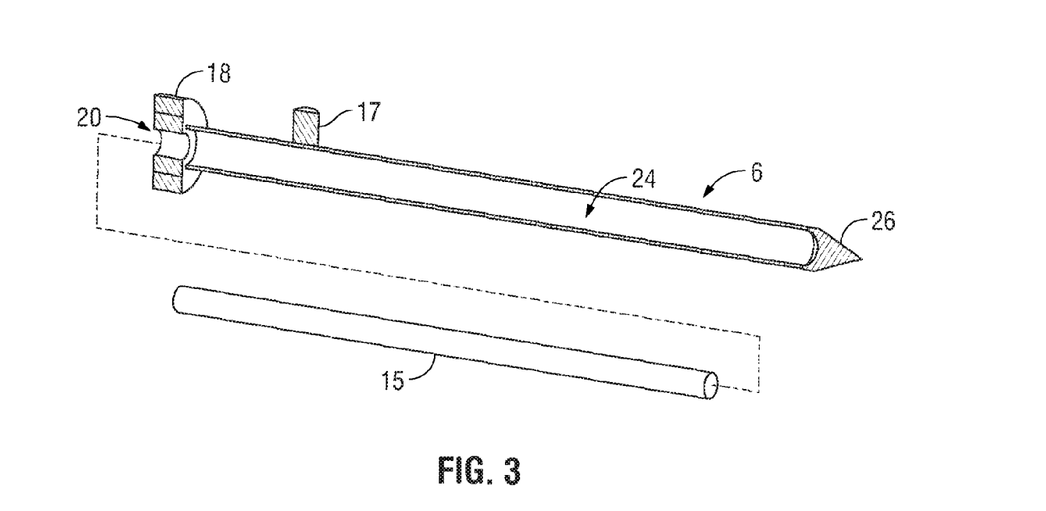
FIG. 3 is a side cut-away view of the introducer catheter depicted in FIG. 2.

Continuing with reference to FIGS. 1A and 1B, and with reference to FIGS. 2-3, catheter 6 is illustrated. Catheter 6 is configured to percutaneously access tissue for adjacent placement thereto and to receive the probe 4 therein. With this purpose in mind, catheter 6 includes a proximal end 12, an elongated body portion or shaft 14 and a distal end 16. In the illustrated embodiment, the catheter includes an inlet/outlet port 17 of suitable dimensions that is operably disposed adjacent the proximal end 12. The inlet/outlet port 17 is in fluid communication with the fluid source 10 (via a supply hose not shown) and a lumen 24 (FIG. 3) of the catheter 6, to be described in greater detail below.

The proximal end 12 is configured to receive the probe 4 therethrough. More particularly, the proximal end 12 is configured to provide a substantially fluid-tight seal between the catheter 6 and the probe 4 when the catheter 6 and the probe 4 are coupled to one another (see FIG. 1B). To this end, a diaphragm 18 of suitable configuration is operably disposed at the proximal end 12 of the catheter 6 (FIGS. 1A-3).

Diaphragm 18 may be made from any suitable material including, but not limited to rubber, plastic, metal, metal alloy, etc. In the illustrated embodiment, the diaphragm 18 is made from rubber. A rubber diaphragm 18 facilitates providing the substantially fluid-tight seal between the catheter 6 and the probe 4 when the catheter 6 and the probe 4 are coupled to one another.

Diaphragm 18 includes a generally annular or circumferential configuration with an opening 20 of suitable configuration (FIG. 3) defined therein. Opening 20 is configured to facilitate receiving the probe 4 therethrough and providing the substantially fluid-tight seal between the catheter 6 and the probe 4. To this end, the opening 20 includes a diameter that is slightly smaller than a diameter of the probe 4. The opening 20 flexes or expands to accommodate the slightly larger diameter of the probe 4. That is, the opening 20 "gives" because of the elasticity attributed to the rubber diaphragm 18. In certain embodiments, it may prove useful to coat the diaphragm 18 (or in some instances the probe 4) with one or more types of lubricious materials, e.g., surgical jelly, PTFE, etc., to decrease the kinetic coefficient of friction between an interior wall of the opening 20 and an exterior surface of the probe 4. The opening 20 extends into the lumen 24 of the shaft 14.

Shaft 14 is suitably proportioned and operably coupled to the diaphragm 18. Shaft 14 includes a generally elongated configuration and may be made from any suitable material. More particularly, shaft 14 is configured such that when the probe 4 is coupled to the catheter 6, the probe 4 is capable of transmitting and/or emitting microwave energy through the shaft 14. With this purpose in mind, shaft 14 is made from a radiofrequency transparent material such as, for example, fiberglass and high temperature composite plastic e.g., polyimide, polyether, ketone, etc.

In certain instances, the shaft 12 and/or catheter 6 are configured to selectively receive a substantially rigid introducer sheath 15 of suitable proportion that is configured to add structural support to the catheter 6 and enhance visibility thereof during image-aided placement of the catheter 6 (FIG. 3). In this instance, the sheath 15 may be inserted into the catheter 6 prior to accessing tissue. When the catheter 6 is positioned adjacent tissue, the sheath 15 may be removed from the catheter 6 and the probe 4 may, subsequently, be inserted into the catheter 6.

In certain instances, the exterior surface of the shaft 14 may include markings that are configured to facilitate placement of the catheter 6 adjacent a tissue specimen. For example, and in certain instances, it may prove useful to provide the exterior surface of the shaft 14 with depth markings 13 (shown in phantom in FIG. 2) for indicating the depth of the inserted catheter in tissue. As noted above, the exterior of the shaft 14 may be coated with one or more lubricious materials for the reasons provided above.

Shaft 14 includes the lumen 24 that is configured such that the probe 4 is movable therein. More particularly, the lumen 24 is configured such that the probe 4 is translatable and rotatable therein; the significance of which to be described in greater detail below. That is, the probe 4 can move distally and proximally within the lumen 24, while maintaining a free rotational orientation thereabout. To this end, the lumen 24 includes diameter that is slightly larger than the diameter of the opening 20 (as best seen in FIG. 3) and a diameter of the probe 4 (as best seen in FIGS. 7A and 7B). Lumen 24 is in fluid communication with the inlet/outlet port 17 for providing a fluid, e.g., chilled saline, therein. The lumen 24 is configured to circulate the fluid from the inlet/outlet port 17 and into the probe 4 (see FIG. 1B in combination with FIG. 6). For illustrative purposes, the fluid flow is illustrated by directional arrows disposed within the lumen 24 and the probe 4. In certain instances, the lumen 24 is configured to circulate the fluid from the probe 4 and into the inlet/outlet port 17. Lumen 24 extends substantially along the length of the shaft 12 and culminates in a generally arcuate contour adjacent the distal end 16 of the catheter 6, see FIGS. 6-7B.

Distal end 16 is configured to pierce tissue such that the catheter 6 may be positioned adjacent (or in some instances into) a tissue specimen, e.g., a tumor. To this end, distal end 16 includes a generally pointed tip 26. Pointed tip 26 may include any shape that is suitable for the purposes intended herein. For illustrative purposes, the pointed tip 26 includes a generally conical shape. Pointed tip 26 may be made from any suitable material. In the illustrated embodiment, pointed tip 26 is made from a material such as metal, ceramic and plastic.

Figure 4A:
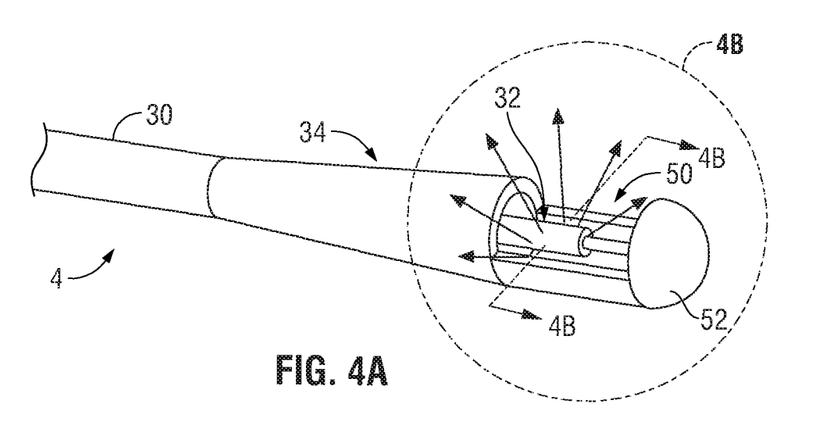
FIG. 4A is a perspective view of a distal end of the directional probe depicted in FIGS. 1A and 1B.
Figure 5:
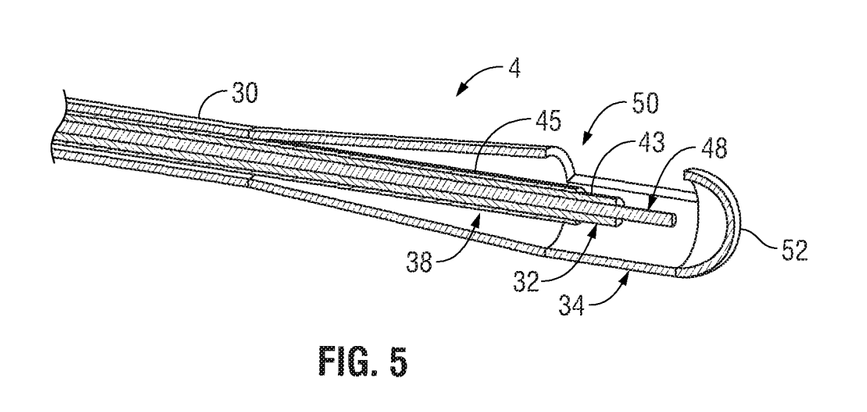
FIG. 5 is a side, cut-away view of the directional probe depicted in FIG. 4A.

With reference again to FIGS. 1A and 1B, and with reference to FIGS. 4A and 5, probe 4 is illustrated. Probe 4 is configured to transmit and/or emit electrosurgical energy, e.g., microwave energy, to target tissue, e.g., a tumor, such that a desired tissue effect may be achieved, e.g., the tumor may be ablated. To this end, probe 4 includes a hub or handle 28 (FIG. 1A), a shaft 30 (FIGS. 1A and 4A) that is configured to support or house an internal coaxial feed or cable 32 (FIGS. 4A and 5), and a conductive distal end or tip 34 (FIGS. 1A, 1B, 4A and 5). In the illustrated embodiment, the probe 4 includes an inlet/outlet port 37 of suitable dimensions that is operably disposed on the handle 28 (FIGS. 1A and 1B). The inlet/outlet port 37 is in fluid communication with the fluid source 10 (via a return hose not shown) and a lumen 38 defined by a shaft 30 (FIGS. 5 and 6), to be described in greater detail below.

With continued reference to FIGS. 1A and 1B, handle 28 is suitably shaped. More particularly, handle 28 may be ergonomically designed to provide a user with an ease of use with respect to rotational and distal and/or proximal positioning within the catheter 6. With this purpose in mind, handle 28 includes a generally circumferential configuration that is configured to support the inlet/outlet port 37 and a connector 42 that couples to a power cable 44 that selectively couples to the microwave generator 8.

Power cable 44 may be any suitable power cable that is capable of conducting electrosurgical energy. Connector 42 provides electrosurgical energy to the conductive distal end 34 via the internal coaxial feed 32 that extends from the proximal end 46 of the probe 4 and includes an inner conductor tip 48 that is operatively disposed adjacent the distal end 34 (as best seen in FIG. 5). As is common in the art, internal coaxial feed 32 includes a dielectric material 43 and an outer conductor 45 surrounding each of the inner conductor tip 48 and dielectric material.

Shaft 30 is operably coupled to the handle 28 and is configured to house or support the internal coaxial feed 32 therein. In the illustrated embodiment, coaxial feed 32 is operably coupled to an internal frame of the shaft 30 by any suitable coupling methods.

Shaft 30 includes a generally elongated configuration with the internal cavity or lumen 38 extending along a length thereof. In the illustrated embodiment, shaft 30 is in fluid communication with the inlet/outlet port 37 via the lumen 38. The lumen 38 channels the fluid, e.g., chilled saline, from the catheter 6 to the inlet/outlet port 37 and ultimately back to the fluid source 10.

Shaft 30 may be made from any suitable material including, but not limited to plastic, metal, metal alloy, etc. In the illustrated embodiment, shaft 30 is made from a lightweight metal, such as, for example, aluminum.

Shaft 30 extends from the proximal end 46 of the probe 4 and includes or couples to the conductive distal end 34 by one or more suitable coupling methods, e.g., brazing, welding, soldering. In certain embodiments, shaft 30 may be monolithically formed with the conductive distal end 34.

With reference again to FIG. 4A, conductive distal end 34 is configured for directing the emission of electrosurgical energy. To this end, conductive distal end 34 includes a generally flared configuration with an aperture or opening 50 of suitable proportion (FIGS. 1A, 4A, and 5-7B) disposed adjacent a distal tip 52.

Figure 6:
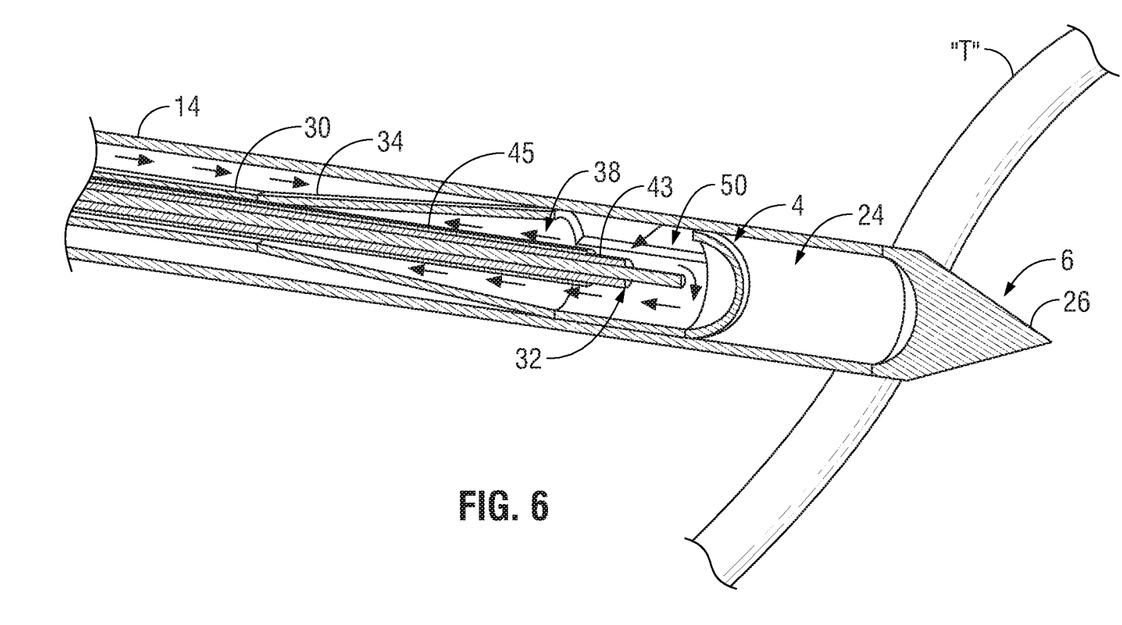
FIG. 6 is a side, cut-away view of a distal end of the directional probe coupled to the introducer catheter depicted in FIG. 1B illustrating fluid flow through the directional probe and the introducer catheter.
Figure 7A:
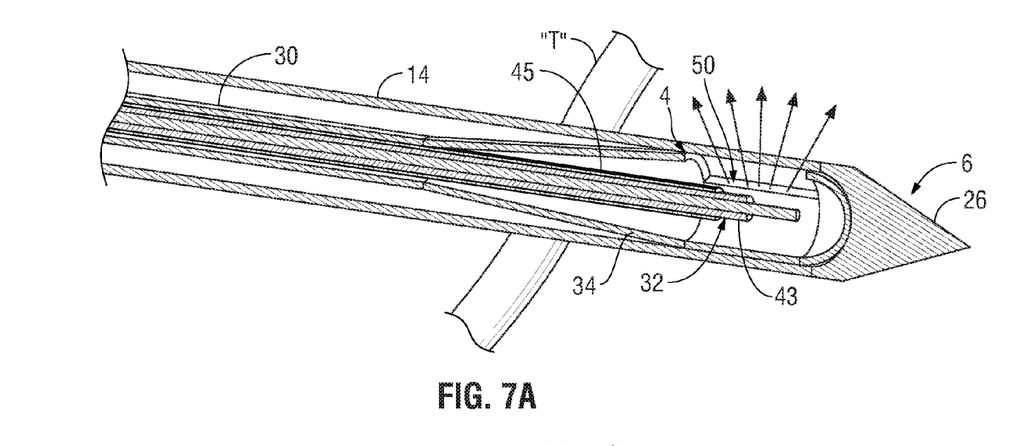
FIGS. 7A and 7B illustrate the directional probe radiating in various directions.
Figure 7B:
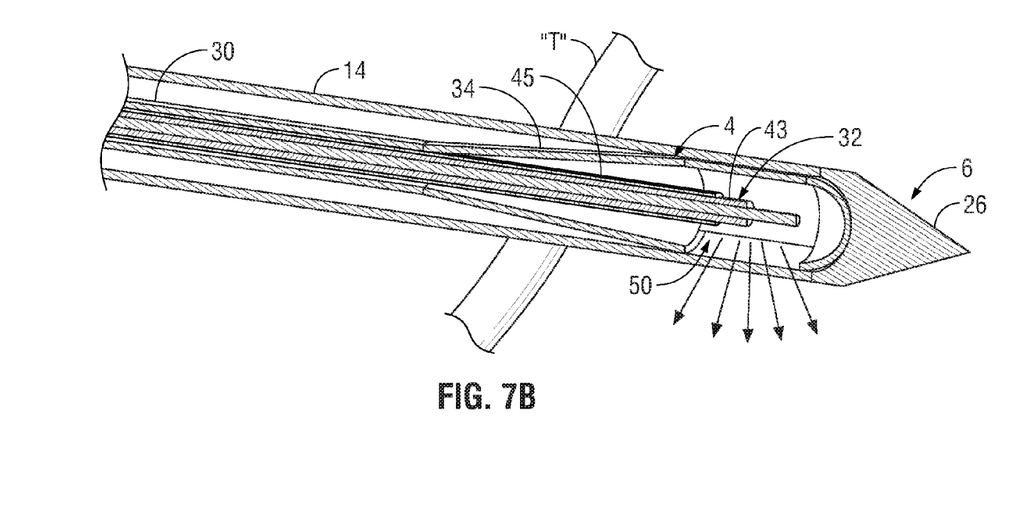

Distal tip 52 includes a generally arcuate configuration that is contoured to match the contour of the distal end of the lumen 24 of the catheter 6 (FIGS. 6 and 7A-7B). Matching the contours of the distal tip 52 and distal end of the lumen 24 facilitates directing fluid flow through the opening 50 when the distal tip 52 has "bottomed out" at or contacted the distal end of the lumen 24. That is, a substantially fluid-tight seal is present at a boundary between the distal tip 52 and distal end of the lumen 24 when the distal tip 52 has "bottomed out" at or contacted the distal end of the lumen 24 and forces the fluid through the opening 50.

Figure 4B:
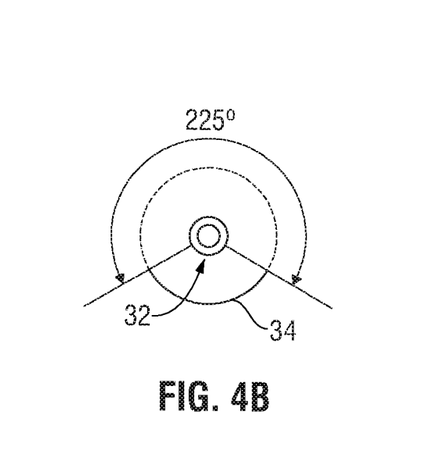
FIG. 4B is a schematic view of the directional probe as depicted in the area of detail of FIG. 4A taken along line segment "4B-4B" illustrating an angle of an opening of the directional probe.
Figure 4B:
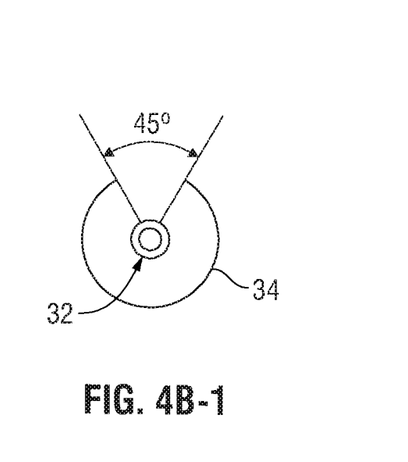

Opening 50 extends along a length of the distal end 34 and includes a generally elongated configuration configured to maximize and/or concentrate electrosurgical energy transmission therefrom. To facilitate directing the electrosurgical energy from conductive distal tip 34 to tissue, the opening 50 is angled (see FIG. 4A in combination with FIG. 4B and 4B$_{-1}$). The angle of the opening 50 ranges from about 45° (FIG. 4B$_{-1}$) to about 250° (FIG. 4B).

Operation of system 2 is described in terms of use of a method for performing an electrosurgical procedure, e.g., a microwave ablation procedure. Catheter 6 with introducer sheath 15 disposed therein is used to percutaneously access underlying tissue (FIG. 6). In certain instances, the imaging guidance system 7 may be utilized to navigate the catheter 6 adjacent a tissue specimen of interest, e.g., a tumor. Once the catheter 6 is in position, the introducer sheath 15 is removed and the probe 4 is introduced into the lumen 24 of the catheter 6 via the opening 20 (FIGS. 1B and 6). A substantially fluid-tight seal is present between the opening 20 and the exterior surface of the shaft 30 of the probe 4 when the probe 4 is introduced into the catheter 6.

Thereafter, microwave generator 8 is activated and microwave energy is transmitted to the inner conductor tip 48 and emitted from the conductive distal tip 34 via the opening 50 (FIG. 7A). The opening 50 and the angle thereof facilitate directing the radiating microwave energy from the opening 50 to specific locations along the target tissue. Under certain surgical environments or conditions, it may prove necessary to treat different locations along the target tissue, in this instance, a user may translate and/or rotate the probe 4 within the lumen 24 of the catheter 6 (FIG. 7B). During the microwave procedure, it may prove useful to cool the inner conductor 48 and or conductive distal tip 34. In this instance, the fluid supply source 10 may be utilized to circulate fluid, e.g., chilled saline, to the inlet/outlet port 17 on the catheter 6 and through the lumen 24 (FIG. 6). The chilled saline returns through the opening 50 of the probe 4 and through the lumen 38 (FIG. 6) to the inlet/outlet port 37 where it is directed back to the fluid supply source via the return hose. As can be appreciated, the circulatory path of the chilled saline may be reversed. That is, the chilled saline may be supplied to the probe 4 and returned to the fluid supply source 10 via the catheter 6.

From the foregoing and with reference to the various figure drawings, those skilled in the art will appreciate that certain modifications can also be made to the present disclosure without departing from the scope of the same. For example, it in certain embodiments, a perforated, non-conductive dielectric window 54 (FIG. 1A) may be operably positioned about the opening 52 to allow fluid flow while providing additional protection to the coaxial feed 32 including the inner conductor tip 48. More particularly, the non-conductive dielectric window 54 functions to protect to the coaxial feed 32 including the inner conductor tip 48 from adjacent tissue structure, bone matter, fluid, or other matter that may pose a possible threat to the coaxial feed 32 including the inner conductor tip 48 during the course of the electrosurgical procedure. For illustrated purposes, in FIG. 1A the non-conductive dielectric window 54 is shown separated from the opening 52. As can be appreciated, the non-conductive dielectric window 54 may be coupled to the opening 54 and/or the distal end 34 via one or more suitable coupling methods, e.g., an adhesive made from an epoxy resin.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of performing an electrosurgical procedure, comprising:

percutaneously accessing tissue with a catheter, the catheter including an open proximal portion and a closed distal portion and defining a lumen therethrough;

positioning a directional microwave antenna probe into the lumen of the catheter such that a longitudinal fluid lumen of the directional microwave antenna probe is in fluid communication with the lumen of the catheter;

transmitting microwave energy to the directional microwave antenna probe such that a desired tissue effect may be achieved;

repositioning the directional microwave antenna probe in the lumen of the catheter; and transmitting the microwave energy to the directional microwave antenna probe.

2. The method according to claim 1, wherein the catheter is made from a radiofrequency transparent material selected from the group consisting of fiberglass and high temperature composite plastic.

3. The method according to claim 2, wherein the distal portion of the catheter is made from a material selected from the group consisting of metal, ceramic and plastic.

4. The method according to claim 2, further comprising providing a fluid to the directional microwave antenna probe via the lumen of the catheter from a fluid port disposed adjacent the proximal portion of the catheter.

5. The method according to claim 1, further comprising providing a fluid-tight seal between the catheter and the directional microwave antenna probe when the catheter and the directional microwave antenna probe are operably coupled to one another via a diaphragm operably coupled to the proximal portion of the catheter.

6. The method according to claim 1, wherein repositioning includes rotating the directional microwave antenna probe within the lumen of the catheter.

7. The method according to claim 1, further comprising selectively coupling the directional microwave antenna probe to the catheter.

8. The method according to claim 1, further comprising coupling the catheter to a rigid introducer sheath.

9. A method of performing an electrosurgical procedure, comprising:

percutaneously accessing tissue with a catheter including an open proximal portion and a closed distal portion configured to access tissue;

positioning a directional microwave antenna probe adapted to connect to a source of electrosurgical energy into the catheter, wherein the directional microwave antenna probe is rotatable within the catheter for directing an emission of electrosurgical energy therefrom to tissue;

coupling the directional microwave antenna probe to the catheter such that a longitudinal fluid lumen of the directional microwave antenna probe is fluidly coupled to a lumen of the catheter; and transmitting electrosurgical energy to the directional microwave antenna probe to treat tissue.

10. The method according to claim 9, wherein the catheter is made from a radiofrequency transparent material selected from the group consisting of fiberglass and high temperature composite plastic.

11. The method according to claim 9, wherein the closed distal portion of the catheter is made from a material selected from the group consisting of metal, ceramic, and plastic.

12. The method according to claim 9, wherein the lumen of the catheter is in fluid communication with a fluid port operably disposed adjacent the open proximal portion of the catheter.

13. The method according to claim 9, further comprising providing a diaphragm at the open proximal portion of the catheter, the diaphragm configured to provide a substantially fluid-tight seal between the catheter and the directional microwave antenna probe when the catheter and the directional microwave antenna probe are operably coupled to one another.

14. The method according to claim 9, wherein percutaneously accessing tissue includes using an imaging device for image-guided placement of the catheter relative to the tissue.

15. The method according to claim 14, wherein the imaging device is selected from the group consisting of a CAT scan device, an ultrasound device, and a magnetic imaging device.

* * * * *